United States Patent [19]

Conte et al.

[11] Patent Number: 5,738,874
[45] Date of Patent: Apr. 14, 1998

[54] PHARMACEUTICAL TABLET CAPABLE OF LIBERATING ONE OR MORE DRUGS AT DIFFERENT RELEASE RATES

[75] Inventors: Ubaldo Conte, Busto Arsizio; Aldo La Manna; Lauretta Maggi, both of Pavia, all of Italy

[73] Assignee: Jagotec AG, Hergiswil, Switzerland

[21] Appl. No.: 406,873

[22] PCT Filed: Sep. 21, 1993

[86] PCT No.: PCT/EP93/02556

§ 371 Date: Mar. 24, 1995

§ 102(e) Date: Mar. 24, 1995

[87] PCT Pub. No.: WO94/06416

PCT Pub. Date: Mar. 31, 1994

[30] Foreign Application Priority Data

Sep. 24, 1992 [IT] Italy ................ MI92A2192

[51] Int. Cl.⁶ .............. A61K 9/22; A61K 9/24; A61K 9/34; A61K 9/36
[52] U.S. Cl. .......... 424/472; 424/468; 424/479; 424/480; 424/481; 424/482
[58] Field of Search ................ 424/464, 472, 424/480, 482, 468, 479, 481

[56] References Cited

U.S. PATENT DOCUMENTS 4,160,020  7/1979  Ayer ................ 424/15
4,839,177  6/1989  Colombo et al. ........ 424/482
5,188,840  2/1993  Iida et al. ............. 424/468

FOREIGN PATENT DOCUMENTS

| 0 167 958 | 1/1986 | European Pat. Off. . |
| 0 226 884 | 7/1987 | European Pat. Off. . |
| 0 432 607 | 6/1991 | European Pat. Off. . |
| 1 022 171 | 3/1966 | United Kingdom . |
| 2 203 338 | 10/1988 | United Kingdom . |
| 9104015 | 4/1991 | WIPO . |

OTHER PUBLICATIONS

Pharmacopeial Forum, May–Jun. 1992, vol. 18, No. 3, pp. 3389–3394.

Primary Examiner—Thurman L. Page
Assistant Examiner—James M. Spear
Attorney, Agent, or Firm—Kenyon & Kenyon

[57] ABSTRACT

Pharmaceutical tablet consisting of a first layer containing one or more drugs with immediate or controlled release formulation, a second layer containing one or more drugs, either equal to or different from the first layer, with slow release formulation, and a low-permeability barrier-type layer coating said second layer or, alternatively, placed between the first and second layer and, if necessary, containing a drug.

7 Claims, 1 Drawing Sheet

PHARMACEUTICAL TABLET CAPABLE OF LIBERATING ONE OR MORE DRUGS AT DIFFERENT RELEASE RATES

This application is a 371 of PCT/EP93/02556 filed Sep. 21, 1993.

PRIOR ART

The development of innovative pharmaceutical forms for drugs administration to humans and animals has lately been a source for considerable research effort in pharmaceutical technology. One of the major innovations in this sector is the targeting of drugs release to a specific sire of treatment and/or the release of said drug at a programmed rate.

The applications thereof are of consequence not only to human and animal health but also to agriculture.

Very many are the pharmaceutical forms already developed and disclosed in patents, which are capable of releasing the drug at zero-order kinetics.

As well known to those skilled in the pharmaceutical art, this means that the pharmaceutical form liberates the drug at a constant rate and over a scheduled period of time. In particular, drug release may occur according to the following empirical relation $$Mt/M_\infty = Kt^n$$

where $Mt/M_\infty$ is the Fraction of released substance, K is a constant depending on the diffusion coefficient in the matrix and n is a constant depending on polymeric chains swelling and relaxation rate in swelling front.

Examples of said pharmaceutical forms are amply documented, e.g. in "Novel drug delivery and its therapeutical application" by L. F. Prescott and W. S. Nimmo, J. Wiley, New York, 1989. Examples refer to pharmaceutical forms that may be administered by different routes, i.e. oral, transdermic, vaginal, and ocular.

Obviously, due to the great importance and wide utilization of oral drug administration, many and diverse embodiments are for gastroenteric administration.

Among the widely known and used embodiments the OROS system., disclosed in U.S. Pat. No. 4,160,020 (1979), should be cited.

A further achievement in the area is the pharmaceutical form disclosed in U.S. Pat. No. 4,839,177 (1989) and in the subsequent U.S. patent application Ser. No. 07/620,577 dated 3rd Dec., 1990 now abandoned. Said patents claim the preparation of pharmaceutical forms for oral administration capable of liberating a drug at a constant release rate, i.e. according to zero-order kinetics.

In particular, the aforesaid patents disclose and claim the preparation of a tablet which, in its simplest form, consists of a hydrophilic matrix containing a drug and suitable excipients allowing the sustained release of the drug.

The drug sustained release is brought about by gelable hydrophilic polymers, which swell by contact with water and/or aqueous fluids, giving a gelled layer wherefrom the drug is liberated according to Fick's type kinetics.

The pharmaceutical form claimed in the aforementioned patents is characterized by the matrix being partly coated with a drug-impermeable barrier consisting of a polymeric film insoluble in water or in an aqueous medium. Alternatively, said barrier consists of polymeric mixtures or granular masses with technological adjuvants, applied by compression (Italian patent application No. 22694/89). The barrier obtained is drug-impermeable for at least 4–8 hrs and, therefore, hinders drug dispensing from the coated surface.

Therefore, the hydrophilic drug is exclusively released from the free area, generally at a constant rate.

However, the prior art does not envisage the possibility of obtaining products capable of releasing one or more drugs at different rates or else of releasing two different drugs sequentially, i.e. releasing the second drug only after releasing the first drug, both being contained in the same pharmaceutical form.

Several treatments require a sequential administration of two drugs and, therefore, involve complex posologic schemes and scrupulous patient's compliance therewith. Obviously, since such compliance is hardly obtainable, the above requirements can often be met only by hospitalized patients, carefully controlled by physicians and paramedical specialists.

As well known, complex therapeutic schemes are reluctantly accepted and scarcely followed by cut-patients, the correct compliance with posologic schemes being inversely proportional to the treatment complexity and to the number of daily administrations, In particular very many are the conditions to be treated with sequentially acting drugs. For example, rheumatic night pain is to be treated with two drug doses, one on pain onset and the other at a later time, or with a pharmaceutical form slowly releasing the second dose so that a sufficiently high plasmatic level be maintained. In these cases, the pharmaceutical form should be capable of releasing the drug at the same rate as drug elimination.

As known, steroid and non-steroid anti-inflammatory agents can induce pyrosis and/or gastric mucosa irritation. A prior protection of the gastric mucosa by agents, such as sucralphate, aluminium glycinate, activated attapulgite or hydrotalcite, followed by the administration of the potentially gastrolesive drug, can increase the patients' tolerance for said drug.

Identical remarks can be made about the antibiotic posology, which usually are to be administered at sequential daily doses.

The same problems are also to be faced with drugs whose active ingredient is a metabolite thereof, the metabolism occurring at different rates in the various organs.

A typical example is L-dopa used in treating Parkinson's disease. In the organism, L-dopa is metabolized to dopamine, which is the drug active ingredient. However, only the unmodified form, i.e. L-dopa, is capable of crossing the blood-brain barrier.

L-dopa is rapidly absorbed into the gastroenteric tract and spreads out in the various organs and tissues, including the CNS. L-dopa has plasmatic half-life of approx. 1 hr and is converted into dopamine mainly by decarboxylation.

L-dopa is rapidly decarboxylated to dopamine also in the gastroenteric tract: hence, the quantity of L-dopa reaching the CNS is extremely low. Furthermore, the presence of excess; dopamine deriving from peripheral decarboxylation in organs external to the CNS may produce massive side effects.

Should drugs inhibiting peripheral decarboxylation, such as benserazide or carbidopa, be administered with or before L-dopa administration, the peripheral conversion of L-dopa into dopamine would be drastically reduced and higher amounts of L-dopa would reach the systemic circulation and the brain, where conversion into dopamine produces the desired therapeutic effect. Thus, much lower L-dopa doses can have a high therapeutic effect and, at the same time, produce lesser side effects.

In such complex pathological situations, the availability of pharmaceutical compositions capable of liberating differ-

3 ent drugs at successive times would solve a therapeutic problem also involving a serious social impact, the treatments being mainly addressed to elderly persons.

SUMMARY

It has been found a new pharmaceutical tablet containing one or more drugs and liberating same at different release rates. This achievement solves the problems encountered so far. Said tablet allows the administration of:

- a single drug, a portion thereof being released within a short time and the remaining portion being released over a longer period;
- two drugs or drug combinations, which are released at different rates. The tablet as per the present invention consists of three layers, i.e.:
- a first layer containing one or more drugs with immediate or controlled release formulation, composed of rapidly swelling and/or soluble and/or erodible polymeric substances by contact with aqueous fluids, and adjuvants;
- a second layer containing one or more drugs, either equal to or different from those of the first layer, with slow release formulation, composed of swelling and/or gelable and/or erodible polymeric substances by contact with aqueous fluids, and adjuvants;
- a low-permeability barrier-type layer coating said second layer, consisting of polymeric materials, adjuvants, plasticizing agents. The tablet may be enteric coated.

DETAILED DESCRIPTION OF THE INVENTION

The following detailed description sets forth the characteristics of and advantages offered by the claimed pharmaceutical tablets, which are capable of releasing one or more drugs at different rates.

Said tablet consists of:

- a first layer containing one or more drugs with immediate or controlled release formulation,
- a second layer containing one or more drugs, either equal to or different from those of the first layer, with slow release formulation, and
- a third layer, which is a low-permeability barrier coating said second layer. This layer serves the purpose of limiting the drug release surface of the adjacent layer.

Preferred embodiments of the invention are shown in FIGS. 1 and 2.

DESCRIPTION OF THE PREFERRED EMBODIMENTS

Figure 1:
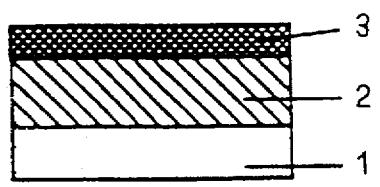
FIG. 1: 1 immediate or controlled release layer; 2 slow release layer; 3 barrier-type layer.

An immediate or controlled release layer formulation consists of rapidly swelling and/or soluble and/or erodible polymeric substances by contact with aqueous fluids and convenient adjuvants.

Said polymeric substances are selected from the group consisting of cross-linked polyvinylpyrrolidone, low- and medium-molecular-weight hydroxypropyl cellulose and hydroxypropyl methylcellulose, cross-linked sodium carboxymethylcellulose, carboxymethyl starch, potassium methacrylate-divinylbenzene copolymer, polyvinyl alcohols, starches, starch derivatives, microcrystalline cellulose and cellulose derivatives, β-cyclodextrin and dextrin derivatives. The amount of said polymeric substances in the layer is 1.0 to 90% by wt., preferably 20 to 70% by wt. Said adjuvants are selected from the categories of substances currently used in the typical pharmaceutical practice, such as diluents, buffers, adsorbents, etc., and in particular search, pregelled starch, calcium phosphate, mannitol, lactose, saccharose, glucose, sorbitol, microcrystalline cellulose, and binding agents, such as gelatin, polyvinylpyrrolidone, methylcellulose, starch solution, ethylcellulose, arabic gum, tragacanth gum.

Other excipients of typical pharmaceutical practice can be used as adjuvants, such as for example magnesium stearate, stearic acid, colloidal silica, glyceryl monostearate, hydrogenated castor oil, waxes, and mono-, bi-, and trisubstituted glycerides.

A slow release layer formulation consists of rapidly swelling and/or gelable and/or erodible polymeric substances by contact with aqueous fluids and convenient adjuvants.

Said polymeric substances are selected from the group consisting of hydroxypropyl methylcellulose having molecular weight from 1,000 to 4,000,000, hydroxypropyl cellulose having molecular weight from 2,000 to 2,000,000, carboxyvinyl polymers, polyvinyl alcohols, glucans, scleroglucans, mannans, xanthans, alginic acid and derivatives thereof, poly(methyl vinyl ethers/maleic anhydride) carboxymethylcellulose and derivatives thereof, ethylcellulose, methylcellulose, and cellulose derivatives.

The amount of said polymeric substances, in respect of the layer total weight, is 5 to 90% by wt. and preferably 5 to 50% by wt.

Various types of all aforesaid polymers, characterized by different physico-chemical, solubility and gelling properties, are commercially available. In particular, various types of hydroxypropyl methylcellulose having different molecular weight (from 1,000 to 4,000,000) and different degree of substitution can be used. They show different characteristics because, depending on the degree of substitution of the polymeric chain, they are either prevailingly erodible or prevailingly gelable. Said adjuvants of the slow release layer are selected from the same group as reported for the immediate or controlled release layer.

The barrier-type layer formulation consists of polymeric substances, adjuvants, and plasticizers.

The polymeric substances of the barrier-type layer are selected from the group consisting of hydroxypropyl methylcellulose having molecular weight From 1,000 to 4,000,000, hydroxypropyl cellulose having molecular weight From 2,000 to 2,000,000, glucans, scleroglucans, mannans, xanthans, carboxymethylcellulose and derivatives thereof, ethylcellulose., methylcellulose. The amount of said polymeric substances, respect of the layer total weight, is 5 to 90% by wt. and preferably 50 to 85% by wt.

Adjuvants are selected From the group consisting of glyceryl monostearate and semisynthetic triglyceride derivatives, semisynthetic glycerides, hydrogenated castor oil, glyceryl palmitostearate, glyceryl behenate, polyvinylpyrrolidone, gelatin, ethylcellulose, methylcellulose, sodium carboxymethylcellulose, as well as other natural or synthetic substances well known to those skilled in the pharmaceutical art, i.e. magnesium stearate, stearic acid, sodium stearate, talc, sodium benzoate, boric acid, polyoxyethylene glycols, and colloidal silica.

As will be illustrated in more detail in the examples reported hereinafter, also diluents, lubricants, buffers, antiblock and gliding agents, and other substances capable of bringing about the desired characteristics in said layer may be used, as described in the following examples.

Plasticizing agents are selected from ths group consisting of hydrogenated castor oil, fatty acids, substituted triglycerides and glycerides, polyoxyethylene glycols and derivatives thereof having a different molecular weight generally ranging from 400 to 60,000. They serve the purpose of making the barrier-type layer as elastic as required.

The polymeric substances used, in combination with the other adjuvants, to prepare the barrier-type layer, make said layer impermeable to the drug of the adjacent layer For at least 4–6 hrs.

Several drugs may be present in the formulation of the three layers of the compressed tablet of the invention. e.g. anti-inflammatory steroids and non-steroid anti-inflammatory drugs (NSAID), such as diclofenac sodium, indomethacin, ibuprofen, ketoprofen, diflunisal, piroxicam, naproxen, flurbiprofen, tolmentin sodium; antibiotics such as ampicillin, amoxycillin, cephradine, clavulanic acid, cephachlor, cephalexin, cloxacillin, erythromycin, their salts and derivatives; urogenital antimicrobial agents, such as nitrofurantoin, nalidixic acid, oxolinic acid, pipemidic acid and its derivatives, sleep producing drugs and tranquilizers, such as diazepam, nitrazepam, flurazepam, oxazepam, chlordiazepoxide, medazepam, lorazepam; drugs for the prevention of anginal and hypertensive attacks, such as diltiazem, trapidil, urapidil, benziodarone, dipiridamole, lidoflazine, naphthydrofuryl oxalate, perhexeline maleate, oxyfedrine hydrochloride; and antihistaminics and/or antiasthmatics, such as ephedrine, terfenadine, theophylline, chlorpheniramine.

The compressed tablets of the invention can be prepared from granular mixtures according to current production techniques: therefore, their production on a commercial-scale can be immediate.

For example, compressed tablets can be obtained by rotary presses operating at a pressure of 1000 to 5000 kg/cm2.

The finished compressed tablets may be further coated with a polymeric film, which passes through the stomach unaltered and is disintegrated in the intestine: the drug can be thus activated and released after reaching the intestinal tract.

The immediate release layer is 0.5 to 5.0 mm thick and has a drug content of 1 to 90% by wt.

The slow release layer is 0.5 to 5.0 mm thick and has a drug content of 0.5 to 80% by wt.

The barrier-like layer is 0.1 to 4.5 mm thick and generally does not contain any drug.

As illustrated in the figures, the barrier-type layer may coat one base of the compressed tablet or the side surface and one base.

The tablets, as per the invention, offer the advantage of releasing the drug or drugs according to a prefixed schedule; therefore lower amounts of drug—in respect of the traditional sustained release tablets—can be administered. Dose dumping is thus avoided and specific therapeutic requirements are met by active ingredients sequential liberation.

The tablets under the invention find very important therapeutic applications, e.g. when one or more drugs are to be administered at different times and when one drug must act immediately and another drug must be long-acting. The Following examples are conveyed by way of indication, not of limitation.

EXAMPLE 1

Figure 2:
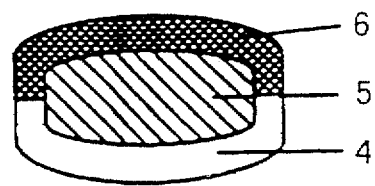
FIG. 2: 4 immediate or controlled release layer; 5 slow release layer; 6 barrier-type layer.

Compressed tablets as per FIG. 2 consisting of a layer 5 containing ephedrine hydrochloride (100 mg) with slow release Formulation, a barrier-type layer 6, and a layer 4 containing further 100 mg ephedrine with immediate release formulation.

| 1-a - Preparation of the granular mass for layer 5 | |
|---|---|
| Ephedrine hydrochloride (B. 15910100, C. Erba) | 100.0 mg |
| Mannitol (C. Erba, Milan, I) | 68.0 mg |
| Hydroxypropyl methylcelluose (Methocel ® K4 M, Colorcon, Orpington, UK) | 20.0 mg |
| Polyvinylpyrrolidone (Plasdone ® K29-32, Gaf Corp., Wayne, NY, USA) | 10.0 mg |
| Magnesium stearate (C. Erba, Milan, I) | 2.0 mg |
| Colloidal silica (Syloid 244, Grace GmbH, Worms, D) | 1.0 mg |
| Total | 201.0 mg |

Ephedrine hydrochloride, mannitol, and hydroxypropyl methylcellulose were pounded in a mortar and wetted with a 20% ethanol solution of polyvinylpyrrolidone. The mixture was; sieved through a 25 mesh sieve screen, even dried to constant weight, sieved again through the same sieve screen, added with the lubricant and silica, and vortex mixed for 10 min. The granular mass obtained A1, which exhibited good free flowing and compacting properties, was compressed as described hereinafter.

| 1-b - Preparation of the granular mass for barrier-like layer (6) | |
|---|---|
| Hydroxypropyl methylcellulose (Methocel ® K100 M, Colorcon, Orpington, UK) | 79.8% |
| Hydogenated castor oil (Cutina HR, Henkel, Düsseldorf, D) | 13.5% |
| Ethylcellulose (Ethocel ® 14 cP, BDH Chem. Ltd., Poole, UK) | 5.0% |
| 20% FCF aluminum lake yellow EEC 110 (Colorcon, Orpington, UK) | 0.5% |
| Magnesium stearate (USP grade, C. Erba, Milan, I) | 1.0% |
| Colloidal silica (Syloid 244, Grace GmbH, Worms, D) | 0.5% |

Hydroxypropyl methylcellulose and hydrogenated castor oil were pounded in a mortar, and the dyeing agent was accurately dispersed. The mixture was wetted with a 5% ethanol solution of ethylcellulose, sieved through a 25 mesh sieve screen, oven dried at 30° C. for 2 hrs approx., sieved again through a 25 mesh sieve screen, added with colloidal silica and Mg stearate, and vortex mixed for 15 min.

The granular mass obtained B1, which exhibited good free flowing and compacting properties, was compressed as described hereinafter.

| 1-c - Preparation of the granular mass for layer (4) | |
|---|---|
| Ephedrine hydrochloride (B. 15910100, C. Erba) | 100.0 mg |
| Lactose (C. Erba, Milan, I) | 40.0 mg |
| Starch from maize (C. Erba, Milan, I) | 60.0 mg |
| Polyvinylpyrrolidone (Plasdone ® K29-32, Gaf Corp., Wayne, NY, USA) | 12.0 mg |
| Carboxymethyl starch (Explotab ® , Edward Mendell Co., Inc., Carmel, NY, USA) | 10.0 mg |
| Cross-linked polyvinylpyrrolidone (Polylasdone XL ® , Gaf Corp., Wayne, NY, USA) | 10.0 mg |
| Magnesium stearate (C. Erba, Milan, I) | 2.0 mg |
| Colloidal silica (Syloid 244, Grace GmbH, Worms, D) | 1.0 mg |
| Total | 235.0 mg |

Ephedrine, lactose, starch from maize were pounded in a mortar and wetted with a 20% ethanol solution of polyvinylpyrrolidone. The mixture was sieved through a 25 mesh sieve screen, oven dried to constant weight, sieved again through the same sieve screen, added with carboxymethyl starch, cross-linked polyvinylpyrrolidone, magnesium stearate, and colloidal silica, and vortex mixed for 15 min.

The granular mass obtained C1, which exhibited good free flowing and compacting properties, was compressed as described hereinafter. 1-d—Preparation of compressed tablets A Dry-Cota (Manesty, Liverpool, UK) rotary press was used for the manufacture of compressed tablets as illustrated in FIG. 2. As well known to those skilled in the art, said press consists of two coupled rotary presses. The press used was equipped with circular concave punches (dia. 8.0 mm: R=10.0 mm) For layer 5 formation and with circular concave punches (dia. 12.0 mm; R=10.0 mm) for layers 4 and 6 formation.

In this Example and in the following ones, R stands for the punch bending radius.

The first press feed hopper was filled with granular mass A1 and the two second press feed hoppers were filled with granular mass B1 and C1, respectively. The first press was set to produce 201 mg layers of granular mass A1 (equalling 100 mg of drug). The first hopper of the second press was set to deliver 230 mg of granular mass B1 while the second hopper was set to deliver 235 mg of granular mass C1 (equalling 100 mg of drug). The operating pressure was ≈2,000 kg/cm2. The compressed tablets obtained averagely weighed 666 mg and contained 200 mg ephedrine hydrochloride.

The obtained tablets were subjected to the dissolution test described below.

1-e—Dissolution test

The tablet release characteristics were evaluated by apparatus 1 (basket) disclosed in USP XXII, operated at 100 rpm. The dissolution fluid was deionized water (500 ml) at 37° C. Drug release was controlled by UV spectrophotometer set at 257 nm, using an automatic sampling and determination system and automatic programme for data processing (Spectracomp 602 of Advanced Products, Milan, Italy). The results obtained are shown in Table 1.

TABLE 1

| Time (min) | released ephedrine (%) |
|---|---|
| 0 | 42.1 |
| 20 | 48.8 |
| 30 | 52.0 |
| 60 | 58.0 |
| 120 | 65.6 |
| 240 | 75.9 |
| 360 | 88.0 |
| 480 | 95.8 |
| 600 | 98.7 |
| 720 | 99.9 |

The above data provide evidence that of the 200 mg of drug contained in the tablet, a portion was released within 20 to 30 min, and the remaining portion within 10 to 12 hrs.

EXAMPLE 2

Compressed tablets as per FIG. 2 consisting of a layer 5 containing ephedrine hydrochloride (100 mg) with slow release formulation, a barrier-type layer 6, and a layer 4 containing 100 mg theophylline with controlled release formulation.

| 2-a - Preparation of the granular mass for layer 5 | |
|---|---|
| Ephedrine hydrochloride (B. 15910100, C. Erba) | 100.0 mg |
| Mannitol (C. Erba, Milan, I) | 68.0 mg |
| Hydroxypropyl methylcellulose (Methocel ® K4 M, Colorcon, Orpington, UK) | 20.0 mg |
| Polyvinylpyrrolidone (Plasdone ® K29-32, Gaf Corp., Wayne, NY, USA) | 10.0 mg |
| Magnesium stearate (C. Erba, Milan, I) | 2.0 mg |
| Colloidal silica (Syloid 244, Grace GmbH, Worms, D) | 1.0 mg |
| Total | 201.0 mg |

Ephedrine hydrochloride, mannitol, and hydroxypropyl methylcellulose were pounded in a mortar and wetted with a 20% ethanol solution of polyvinylpyrrolidone. The mixture was sieved through a 25 mesh sieve screen, oven dried to constant weight, sieved again through the same sieve screen, added with the lubricant and silica, and vortex mixed for 10 min.

The granular mass obtained A2, which exhibited good free flowing and compacting properties, was compressed as described hereinafter.

| 2-b - Preparation of the granular mass for barrier-like layer (6) | |
|---|---|
| Hydroxypropyl methylcellulose (Methocel ® K100 M, Colorcon, Orpington, UK) | 79.8% |
| Hydrogenated castor oil (Cutina HR, Henkel, Düsseldorf, D) | 13.5% |
| Ethylcellulose (Ethocel ® 14 cP, BDH Chem. Ltd., Poole, UK) | 5.0 |
| 20% FCF aluminium lake yellow EEC 110 (Colorcon, Orpington, UK) | 0.5% |
| Magnesium stearate (USP grade, C. Erba, Milan, I) | 1.0% |
| Colloidal silica (Syloid 244, Grace GmbH, Worms, D) | 0.5% |

Hydroxypropyl methylcellulose and hydrogenated castor oil were pounded in a mortar, and the dyeing agent was accurately dispersed. The mixture was wetted with s 5% ethanol solution of ethylcellulose, sieved through a 25 mesh sieve screen, oven dried at 30° C. for 2 hrs approx., sieved again through a 25 mesh sieve screen, added with colloidal silica and Mg stearate, and vortex mixed for 15 min.

The granular mass obtained B2, which exhibited good free flowing and compacting properties, was compressed as described hereinafter.

| 2-c - Preparation of the granular mass for layer 4 | |
|---|---|
| Anhydrous theophylline (C. Erba, Milan, I) | 100.0 mg |
| Lactose (C. Erba, Milan, I) | 50.0 mg |
| Hydroxypropyl methylcellulose (Methocel ® E5 Premium, Colorcon, Orpington, UK) | 60.0 mg |
| Polyvinylpyrrolidone (Plasdone ® K29-32, Gaf Corp., Wayne, NY, USA) | 12.0 mg |
| Magnesium stearate (C. Erba, Milan, I) | 2.0 mg |
| Colloidal silica (Syloid 244, Grace GmbH, Worms, D) | 1.0 mg |
| Total | 225.0 mg |

Theophylline, lactose, hydroxypropyl methylcellulose were pounded in a mortar and wetted with a 20% ethanol solution of polyvinylpyrrolidone. The mixture was sieved through a 25 mesh sieve screen, oven dried to constant weight, sieved again through the same sieve screen, added with magnesium stearate and colloidal silica, and vortex mixed for 15 min. The C2 granular mass obtained, which exhibited good free flowing and compacting properties, was compressed as described hereinafter.

2-d—Preparation of compressed tablets

A Dry-Cora (Manesty, Liverpool, UK) rotary press as described in Example 1 was used for the manufacture of compressed tablets as illustrated in FIG. 2.

The first press feed hopper was filled with granular mass A2 and the two second press feed hoppers were filled with granular mass B2 and C2, respectively. The first press was set to produce 201 mg layers of granular mass A2, equalling 100 mg of drug (ephedrine). The first hopper of the second press was set to deliver 230 mg of granular mass B2 while the second hopper of the second press was set to deliver 225 mg granular mass C2, equalling 100 mg of drug (theophylline). The operating pressure was ≈2,000 kg/cm2. The compressed tablets obtained averagely weighed 656 mg and contained 100 mg ephedrine hydrochloride and 100 mg theophylline.

The obtained tablets were subjected to the dissolution test described below.

2-e—Dissolution test

The tablet release characteristics of the two drugs were evaluated by apparatus 1 (basket) disclosed in USP XXII, operated at 100 rpm. The dissolution fluid was deionized water (1000 ml) at 37° C. Drug release was controlled by UV spectrophotometer set, respectively, at 257 nm for ephedrine and at 271 nm for theophylline, using an automatic sampling and determination system and an automatic programme for data processing (Spectracomp 602 of Advanced Products, Milan, Italy), or a chromatographic control method (HPLC). The results obtained are shown in Table 2.

TABLE 2

| Time (min) | released theophylline (%) | released ephedrine (%) |
|---|---|---|
| 15 | 21.5 | — |
| 30 | 47.0 | — |
| 60 | 84.1 | — |
| 90 | 96.4 | 2.6 |
| 120 | 100.8 | 10.3 |
| 240 | — | 41.2 |
| 360 | — | 66.5 |
| 480 | — | 85.8 |
| 600 | — | 94.7 |
| 720 | — | 99.9 |

The above data provide evidence that the drug release from layer 5 (ephedrine) occurred only after the drug controlled release from layer 4 (theophylline), which took 2 hrs approx.

EXAMPLE 3

Compressed tablets as per FIG. 2 consisting of a layer 5 containing ketoprofen (100 mg) with slow release formulation, a barrier-type layer 6, and a layer 4 containing further 100 ketoprofen with immediate release formulation.

| 3-a - Preparation of the granular mass for layer (5) | |
|---|---|
| Ketoprofen (Soc. It. Med., Scandicci, Firenze, I) | 100.0 mg |
| Hydroxypropyl methylcellulose (Methocel ® K4 M, Colorcon, Orpington, UK) | 75.0 mg |
| Mannitol (C. Erba, Milan, I) | 40.0 mg |
| Polyvinylpyrrolidone (Plasdone ® K29-32, Gaf Corp., Wayne, NY, USA) | 14.5 mg |
| Magnesium stearate (C. Erba, Milan, I) | 1.0 mg |
| Colloidal silica (Syloid 244, Grace GmbH, Worms, D) | 0.5 mg |
| Total | 231.0 mg |

Ketoprofen, mannitol, and hydroxypropyl methylcellulose were pounded in a mortar and wetted with a 20% ethanol solution of polyvinylpyrrolidone. The mixture was sieved through a 25 mesh sieve screen, oven dried to constant weight, sieved again through the same sieve screen, added with magnesium stearate and colloidal silica, and vortex mixed for 15 min.

The A3 granular mass obtained, which exhibited good free flowing and compacting properties, was compressed as described hereinafter.

| 3-b - Preparation of the granular mass for barrier-like layer 6 | |
|---|---|
| Hydroxypropyl methylcellulose (Methocel ® K100 M, Colorcon, Orpington, UK) | 79.8% |
| Hydrogenated castor oil (Cutina HR, Henkel, Düsseldorf, D) | 13.5% |
| Ethylcellulose (Ethocel ® 14 cP, BDH Chem. Ltd., Poole, UK) | 5.0% |
| 20% FCF aluminium lake yellow EEC 110 (Colorcon, Orpington, UK) | 0.5% |
| Magnesium stearate (USP grade, C. Erba, Milan, I) | 1.0% |
| Colloidal silica (Syloid 244, Grace GmbH, Worms, D) | 0.5% |

Hydroxypropyl methylcellulose and hydrogenated castor oil were pounded in a mortar, and the dyeing agent was accurately dispersed. The mixture was wetted with a 5% ethanol solution of ethylcellulose, sieved through a 25 mesh sieve screen, oven dried at 30° C. for 2 hrs approx., sieved again through a 25 mesh sieve screen, added with sieved colloidal silica and Mg stearate, and vortex mixed for 15 min.

The B3 granular mass obtained, which exhibited good free flowing and compacting properties, was compressed as described hereinafter.

| 3-c - Preparation of the granular mass for layer 4 | |
|---|---|
| Ketoprofen (Soc. It. Med., Scandicci, Firenze, I) | 100.0 mg |
| Starch from maize (C. Erba, Milan, I) | 80.0 mg |
| Methylcellulose (500–600 cps BDH Chemicals Ltd., Poole, UK) | 1.0 mg |
| Carboxymethyl starch (Explotab ® , Edward Mendell Co. Inc., Carmel, NY, USA) | 19.5 mg |
| Cross-linked polyvinylpyrrolidone (Polylasdone XL ® , Gaf Corp., Wayne, NY, USA) | 20.0 mg |
| Magnesium stearate (C. Erba, Milan, I) | 1.0 mg |
| Colloidal silica (Syloid 244, Grace GmbH, Worms, D) | 0.5 mg |
| Total | 222.0 mg |

Ketoprofen and starch from maize were pounded in a mortar and wetted with a 1% methylcellulose aqueous solution. The mixture was sieved through a 25 mesh sieve screen, oven dried to constant weight, and sieved again through the same sieve screen, added with carboxymethyl starch, cross-linked polyvinylpyrrolidone, magnesium stearate, and colloidal silica, and vortex mixed for 15 min.

The C3 granular mass obtained, which exhibited good free flowing and compacting properties, was compressed as described hereinafter. 3-d—Preparation of compressed tablets A Dry-Cora (Manesty, Liverpool, UK) rotary press as described in Example 1 was used for the manufacture of compressed tablets as illustrated in FIG. 2. The first press feed hopper was filled with the granular mass described under 3-a granular mass A3 and the two second press feed hoppers were filled with the granular masses described under 3-b B3 and 3-c C3, respectively. The first press was set to produce 231 mg layers of granular mass A3, equalling 100 mg of drug (ketoprofen). The first hopper of the second press was set to deliver 230 mg of granular mass B3 while the second hopper of the second press was set to deliver 222 me of granular mass C3 (equalling 100 mg of drug). The operating pressure was ≈2,000 kg/cm2. The compressed tablets obtained averagely weighed 683 mg and contained 200 mg ketoprofen.

The obtained tablets were subjected to the dissolution test described below.

3-e—Dissolution test

The tablet release characteristics were evaluated by apparatus 1 (basket) disclosed in USP XXII, operated at 100 rpm. The dissolution fluid was simulated intestinal fluid (USP XXII) (1000 ml) without enzymes at 37° C. Drug release was controlled by UV spectrophotometer set at 264 nm, using an automatic sampling and determination system and an automatic programme for data processing (Spectracomp 602 of Advanced Products, Milan, Italy). The results obtained are shown in Table 3.

TABLE 3

| Time (hrs) | released ketoprofen (%) |
|---|---|
| 0.5 | 48.2 |
| 1 | 49.2 |
| 2 | 50.2 |
| 4 | 53.2 |
| 6 | 58.3 |
| 8 | 62.1 |
| 10 | 69.8 |
| 14 | 78.6 |
| 18 | 89.3 |
| 24 | 99.6 |

The above data provide evidence that 50% of drug was released within 30 min and the remaining 50% within 24 hrs approx.

EXAMPLE 4

Compressed tablets having the characteristics shown in per FIG. 1 consisting of a layer 1 containing the drug (ephedrine hydrochloride) with immediate release formulation, a layer 2 containing the same drug with slow release formulation, and a barrier-type layer 3 limiting the drug release from the layers underneath.

For tablet preparation, three different granular mass types were used, having respectively the following characteristics:

| 4-a - Granular mass for layer 1 | |
|---|---|
| Ephedrine hydrochloride (B. 15910100, C. Erba) | 100.0 mg |
| Lactose (C. Erba, Milan, I) | 40.0 mg |
| Starch from maize (C. Erba, Milan, I) | 60.0 mg |
| Polyvinylpyrrolidone (Plasdone ® D29-32, Gaf Corp., Wayne, NY, USA) | 12.0 mg |
| Carboxymethyl starch (Explotab ®, Edward Mendell Co. Inc., Carmel, NY, USA) | 10.0 mg |
| Cross-linked polyvinylpyrrolidone (Polylasdone XL ®, Gaf Corp., Wayne, NY, USA) | 10.0 mg |
| Magnesium stearate (C. Erba, Milan, I) | 2.0 mg |
| Colloidal silica (Syloid 244, Grace GmbH, Worms, D) | 1.0 mg |
| Total | 235.0 mg |

Ephedrine, lactose, and snatch from maize were pounded in a mortar and wetted with a 20% ethanol solution of polyvinylpyrrolidone. The mixture was sieved through a 25 mesh sieve screen, oven dried to constant weight, sieved again through the same sieve screen, added with carboxymethyl starch, cross-linked polyvinylpyrrolidone, magnesium stearate, and colloidal silica, and vortex mixed for 15 min.

The granular mass obtained A4, which exhibited good free flowing and compacting properties, was compressed as described

| 4-b - Granular mass for layer 2 | |
|---|---|
| Ephedrine hydrochloride (B. 15910100, C. Erba) | 100.0 mg |
| Mannitol (C. Erba, Milan, I) | 68.0 mg |
| Hydroxypropyl methylcellulose (Methocel ® K4 M, Colorcon, Orpington, UK) | 20.0 mg |
| Polyvinylpyrrolidone (Plasdone ® K29-32, Gaf Corp., Wayne, NY, USA) | 10.0 mg |
| Magnesium stearate (C. Erba, Milan, I) | 2.0 mg |
| Colloidal silica (Syloid 244, Grace GmbH, Worms, D) | 1.0 mg |
| Total | 201.0 mg |

Ephedrine hydrochloride, mannitol, and hydroxypropyl methylcellulose were pounded in a mortar, wetted with a 20% ethanol solution of vinylpyrrolidone, sieved through a 25 mesh sieve screen, oven dried to constant weight, sieved again through the same sieve screen, added with the lubricant and silica, and vortex mixed for 10 min.

The granular mass obtained C4, which exhibited good free flowing and compacting properties, was compressed as described hereinafter.

| 4-c - Granular mass for barrier-like layer 3 | |
|---|---|
| Hydroxypropyl methylcellulose (Methocel ® K100 M, Colorcon, Orpington, UK) | 79.8% |
| Hydrogenated castor oil (Cutina HR, Henkel, Düsseldorf, D) | 13.5% |
| Ethylcellulose (Ethocel ® 14 cP, BDH Chem. Ltd., Poole, UK) | 5.0% |
| 20% FCF aluminium lake yellow EEC 110 (Colorcon, Orpington, UK) | 0.5% |
| Magnesium stearate (USP grade, C. Erba, Milan, I) | 1.0% |
| Colloidal silica (Syloid 244, Grace GmbH, Worms, D) | 0.5% |

Hydroxypropyl methylcellulose and hydrogenated castor oil were pounded in a mortar, and the dyeing agent was accurately dispersed. The mixture was wetted with a 5% ethanol solution of ethylcellulose, sieved through a 25 mesh sieve screen, oven dried at 30° C. for 2 hrs approx., sieved again through a 25 mesh sieve screen, added with colloidal silica and Mg stargazed, and vortex mixed for 15 min.

The granular mass obtained B4, which exhibited good free flowing and compacting properties, was compressed as described hereinafter.

The three granular masses obtained as described above were loaded into the three feed hoppers of a rotary press fit fop producing three-layer tablets, equipped with circular flat punches 10 mm in diameter (Layer-press, Manesty, Liverpool, UK). The press was set to feed the first loading station with 235 mg of granular mass A4, equalling 100 mg of drug, the second loading station with 201 mg of granular mass C4, equalling 100 mg of drug, and the third loading station with 60 mg of granular mass B4. Said amount of B4 proved to be sufficient to produce a polymeric layer drug-impermeable for over 4 to 6 hrs.

Therefore, the press automatically produces a three-layer tablet, the first layer releasing 100 mg ephedrine within su short time and the second layer releasing 100 mg ephedrine within a longer time.

The preparation was controlled by dissolution tests carried out with the equipment (basket, 100 rpm) and according to the method disclosed in USP XXII. The dissolution fluid was distilled water at 37° C.

TABLE 4

| Time (min) | released ephedrine hydrochloride (mg) |
|---|---|
| 0 | 0 |
| 5 | 100 |
| 15 | 125 |
| 30 | 130 |
| 60 | 145 |
| 120 | 170 |
| 180 | 180 |
| 360 | 200 |

The above data provide evidence that the tablet can release a first portion (100 mg) immediately and the remaining portion (100 mg) gradually. For the purpose of comparison and of evaluating the efficiency of layer 3, a compressed tablet without said layer and, therefore, consisting only of layers 1 and 2 was also prepared.

Dissolution test carried out according to the procedure described above gave the following results.

TABLE 4A

| Time (min) | released ephedrine hydrochloride (mg) |
|---|---|
| 0 | 0 |
| 5 | 100 |
| 15 | 140 |
| 30 | 155 |
| 60 | 180 |
| 120 | 195 |
| 150 | 200 |

A comparison between these data and those previously reported shows that the release of the second drug portion from the compressed tablet was considerably slowed down by the barrier-type layer.

EXAMPLE 5

Compressed tablets as shown in FIG. 2 consisting of a layer 5 containing ketoprofen (100 mg) with low release formulation, a barrier-type layer 6, and a layer 4 containing 200 mg sucralphate with immediate release formulation.

| a - Preparation of the granular mass for layer 5 | |
|---|---|
| Ketoprofen (Soc. It. Med., Scandicci. Firenze, I) | 100.0 mg |
| Hydroxypropyl methylcellulose (Methocel ® K4 M, Colorcon, Orpington, UK) | 75.0 mg |
| Mannitol (C. Erba, Milan, I) | 40.0 mg |
| Polyvinylpyrrolidone (Plasdone ® K29-32, Gaf Corp., Wayne, NY, USA) | 14.5 mg |
| Magnesium stearate (C. Erba, Milan, I) | 1.0 mg |
| Colloidal silica (Syloid 244, Grace GmbH, Worms, D) | 0.5 mg |
| Total | 231.0 mg |

Ketoprofen, mannitol, and hydroxypropyl cellulose were pounded in a mortar and wetted with a 20% ethanol solution of polyvinylpyrrolidone. The mixture was sieved through a 25 mesh sieve screen, oven dried to constant weight, sieved again through the same sieve screen, added with magnesium stearate and colloidal silica, and vortex mixed for 15 min.

The granular mass obtained A5, which exhibited good free flowing and compacting properties, was compressed as described hereinafter.

| 5-b - Preparation of the granular mass for barrier-like layer 6 | |
|---|---|
| Hydroxypropyl methycellulose (Methocel ® E5, Colorcon, Orpington, UK) | 79.8% |
| Hydrogenated castor oil (Cutina HR, Henkel, Düsseldorf, D) | 13.5% |
| Ethylcellulose (Ethocel ® 14 cP, BDH Chem. Ltd., Poole, UK) | 5.0% |
| 20% FCF aluminium lake yellow EEC 110 (Colorcon, Orpington, UK) | 0.5% |
| Magnesium stearate (USP grade, C. Erba, Milan, I) | 1.0% |
| Colloidal silica (Syloid 244, Grace GmbH, Worms, D) | 0.5% |

Hydroxypropyl methylcellulose and hydrogenated castor oil were pounded in a mortar, and the dyeing agent was accurately dispersed. The mixture was wetted with a 5% ethanol solution of ethylcellulose, sieved through a 25 mesh sieve screen, oven dried at 30° C. for 2 hrs approx., sieved again through a 25 mesh sieve screen, added with colloidal silica and Mg stearate, and vortex mixed For 15 min.

The granular mass obtained B5, which exhibited good free flowing and compacting properties, was compressed as described hereinafter.

| 5-c - Preparation of the granular mass for layer 4 | |
|---|---|
| Sucralphate | 200.0 mg |
| Starch from maize (C. Erba, Milan, I) | 100.0 mg |
| Polyvinylpyrrolidone (Plasdone ® K29-32, Gaf Corp., Wayne, NY, USA) | 15.0 mg |
| Carboxymethyl starch (Explotab ® , Edward Mendell Co. Inc., Carmel, NY, USA) | 25.0 mg |
| Talc (C. Erba, Milan, I) | 4.0 mg |
| Magnesium stearate (C. Erba, Milan, I) | 2.0 mg |
| Total | 346.0 mg |

Sucralphate and starch from maize were pounded in a mortar and wetted with a 20% alcohol solution of polyvinylpyrrolidone. The mixture was sieved through a 25 mesh sieve screen, oven dried to constant weight, sieved again through the same sieve screen, added with carboxymethyl starch, talc, and magnesium stearate, and vortex mixed for 15 min.

The granular mass obtained C5, which exhibited good free flowing and compacting properties, was compressed as described hereinafter.

5-d—Preparation of finished systems (by compression)

A Dry-Cota (Manesty, Liverpool, UK) rotary press as described in Example 1 was used for the manufacture of compressed tablets as illustrated in FIG. 2. The first press feed hopper filled with granular mass A5 and the two second press feed hoppers were filled with granular mass B5 and C5, respectively. The first press was set to produce 231 mg layers (equalling 100 mg of drug). The first hopper of the second press was set to deliver 230 mg of granular mass B5 and the second hopper of the second press was set to deliver 346 mg of granular mass C5 (equalling 200 mg of drug). The operating pressure was ≈2,000 kg/cm2.

The compressed tablets obtained averagely weighed 807 mg and contained 100 mg ketoprofen and 200 mg sucralphate.

The obtained tablets were subjected to the dissolution test described below.

5-e—Disintegration and dissolution test

The tablet release characteristics of the two drugs were evaluated. The time of disintegration of the layer containing sucralphate was determined by an ad-hoc apparatus according to USP. Ketoprofen dissolution test was carried out with apparatus 1 (basket, 100 rpm) described in USP XXII, in 1000 ml simulated intestinal fluid (USP XXII) without enzymes at 37° C. Drug (ketoprofen) release was controlled by UV spectrophotometer set at 26 nm, using an automatic sampling and determination system and an automatic programme for data processing (Spectracomp 602 of Advanced Products, Milan, Italy).

As far as ketoprofen is concerned, the results obtained are shown in Table 5.

TABLE 5

Time of disintegration of the layer containing sucralphate: 5 min.
Ketoprofen dissolution test:

| Time (h) | released ketoprofen (%) |
|---|---|
| 1 | 2.5 |
| 2 | 4.7 |
| 4 | 10.5 |
| 6 | 21.7 |
| 8 | 34.6 |
| 10 | 46.6 |
| 14 | 64.5 |
| 18 | 88.9 |
| 24 | 100.1 |

The results provide evidence that ketoprofen was released in 24 hrs approx. The amount of sucralphate released was determined according to the method described in Pharmacopoeial Forum, May-June 1992. p. 389: the results obtained proved That sucralphate was fast released.

EXAMPLE 6

Compressed tablets as shown in FIG. 1 consisting of a layer 1 containing amoxycillin trihydrate with immediate release formulation, a layer 2 containing the same drug as layer 1 with slow release formulation, and a barrier-type layer 3 serving the purpose of slowing down drug release from the layer underneath.

Three different granular mass types having the following characteristics were used:

| 6-a - Mixture for the preparation of layer 1 | |
|---|---|
| Amoxycillin trihydrate (equalling 250 mg amoxycillin) (Ribon, Milan, I) | 287.0 mg |
| Microcrystalline cellulose (Avicel PH 102) | 100.0 mg |
| Carboxymethyl starch (Explotab ® , Edward Mendell Co. Inc., Carmel, NY, USA) | 20.0 mg |
| Talc (C. Erba, Milan, I) | 40.0 mg |
| Magnesium stearate (C. Erba, Milan, I) | 15.0 mg |
| Colloidal silica (Syloid 244, Grace GmbH, Worms, D) | 10.0 mg |
| Total | 452.0 mg |

Amoxycillin trihydrate, microcrystalline cellulose, carboxymethyl starch, talc, magnesium stearate, and colloidal silica were vortex mixed for 15 min. The mixture obtained A6, which exhibited good free flowing and good compacting by direct compression, was compressed as described hereinafter.

| 6-b - Granular mass for layer 2 preparation | |
|---|---|
| Amoxycillin trihydrate (equalling 250 mg amoxycillin) (Ribon, Milan, I) | 287.0 mg |

-continued

| 6-b - Granular mass for layer 2 preparation | |
|---|---|
| Hydroxypropyl methylcellulose (Methocel ® K15 M, Colorcon, Orpington, UK) | 100.0 mg |
| Mannitol (C. Erba, Milan, I) | 50.0 mg |
| Polyvinylpyrrolidone (Plasdone ® K29-32, Gaf Corp., Wayne, NY, USA) | 20.0 mg |
| Talc (C. Erba, Milan, I) | 5.0 mg |
| Magnesium stearate (C. Erba, Milan, I) | 2.0 mg |
| Total | 464.0 mg |

Amoxycillin trihydrate, mannitol, and hydroxypropyl methylcellulose were pounded in a mortar, was wetted with a 10% ethanol solution of polyvinylpyrrolidone, sieved through a 25 mesh sieve screen, oven dried to constant weight, sieved again through the same sieve screen, added with Mg stearate and talc, and vortex mixed for 15 min.

The granular mass obtained C6, which exhibited good free flowing and compacting properties, was compressed as described hereinafter.

| 6-c - Granular mass for barrier-type layer 3 | |
|---|---|
| Hydroxypropyl methylcellulose (Methocel ® K100 M, Colorcon, Orpington, UK) | 74.6% |
| Hydrogenated castor oil (Cutina HR, Henkel, Düsseldorf, D) | 15.4% |
| Ethylcellulose (Ethocel ® 14 cP, BDH Chem. Ltd., Poole, UK) | 8.0% |
| FCF blue EEC 133 (Colorcon, Orpington, UK) | 0.5% |
| Magnesium stearate (USP grade, C. Erba, Milan, I) | 1.0% |
| Colloidal silica (Syloid 244, Grace GmbH, Worms, D) | 0.5% |

Hydroxypropyl methylcellulose and hydrogenated castor oil were pounded in a mortar, and the dyeing agent was accurately dispersed. The mixture was wetted with a 5% ethanol solution of ethylcellulose, sieved through a 25 mesh sieve screen, oven dried at 30° C. for 2 hrs approx., sieved again through a 25 mesh sieve screen, added with sieved colloidal silica and Mg stearate, and vortex mixed for 15 min.

The granular mass obtained B6, which exhibited good free flowing and compacting properties, was compressed as described hereinafter.

The three granular masses obtained as described above were loaded into three feed hoppers of a rotary press capable of producing three-layer tablets, equipped with oval concave punches (9.0×19.0 mm: R=10.0 mm) (Layer-press, Manesty, Liverpool, UK).

The press was set to feed the first loading station with 452 mg of mixture A6, equalling 250 mg of drug, the second loading station with 464 mg of granular mass C6, equalling 250 mg of drug, and the third loading station with 112 mg of granular mass B6. Said amount of B6 proved to be sufficient to produce a polymeric layer drug-impermeable for over 4 to 6 hrs.

Therefore, the press can automatically produce a pharmaceutical form consisting of a three-layer compressed tablet, the first layer releasing 250 mg amoxycillin in within a short time and the second layer releasing 250 mg amoxycillin within a longer time. The preparation was controlled by dissolution tests carried out with the equipment (basket, 100 rpm) and according to the method disclosed in USP XXII. The dissolution fluid was 0.1N HCl (1000 ml) at 37° C. Drug release was controlled by UV spectrophotometer set an 230 nm, using an automatic sampling and determination system and an automatic programme for data processing (Spectracomp 602 of Advanced Products, Milan, Italy).

The results obtained are shown in Table 6.

TABLE 6

| Time (min) | released amoxycillin (%) |
|---|---|
| 5 | 55.2 |
| 30 | 62.1 |
| 60 | 66.2 |
| 120 | 71.4 |
| 240 | 79.2 |
| 360 | 85.7 |
| 480 | 91.5 |
| 720 | 100.1 |

In this case, the first drug portion was released immediately (in 5 min) and the second portion in 12 hrs approx.

We claim:

1. Pharmaceutical compressed tablet capable of releasing one or more drugs at two different steps, consisting of three layers of discoidal shape, obtained by compression of the mixture of the granular components and wherein:

a first layer, which carries out a first release step, contains one or more drugs with immediate or controlled release formulation, comprising polymeric substances which swell or solubilize when contacted with aqueous liquids, said polymeric substances selected from the group consisting of cross-linked polyvinylpyrrolidone, low and medium molecular weight hydroxypropyl cellulose and hydroxypropyl methylcellulose, cross-linked sodium carboxymethylcellulose, carboxymethyl starch, potassium methacrylate-divinylbenzene copolymer, polyvinyl alcohols, starches, microcrystalline cellulose and β-cyclodextrin, said polymeric substances amounting to from about 1% to about 90% by weight of said first layer;

a second layer adjacent to the first layer and carrying out a second release step, contains one or more drugs, either equal to or different from those of the first layer with slow release formulation, comprising polymeric substances which swell or erode or are gellable when contacted with aqueous liquids said polymeric substances selected from the group consisting of hydroxypropyl methylcellulose having a molecular weight from 1000 to 4,000,000, hydroxypropyl cellulose having molecular weight from 2,000 to 2,000,000, carboxyvinyl polymers, polyvinyl alcohols, glucans, scleroglucans, mannans, xanthans, alginic acid, and carboxymethylcellulose, said polymeric substances amounting to from about 5% to about 90% by weight of said second layer; and a third barrier layer having low permeability and coating the free surface of said second layer and comprising polymeric substances selected from the group consisting of hydroxypropyl methylcellulose having a molecular weight from 1,000 to 4,000,000, hydroxypropyl cellulose having molecular weight from 2,000 to 2,000,000, glucans, scleroglucans, mannans, xanthans, carboxymethylcellulose, ethylcellulose, and methylcellulose said polymeric substances amounting to from about 5% to about 90% by weight of said third layer.

2. The compressed tablet according to claim 1 wherein barrier layer coats partially the second layer, the remaining surface of second layer being covered by first layer.

3. The compressed tablet according to claim 1, wherein said first layer is 0.5 to 5 mm thick.

4. The compressed tablet according to claim 1, wherein said second layer is 0.5 to 5 mm thick.

5. The compressed tablet according to claim 1, wherein said barrier layer is 0.1 to 4.5 mm thick.

6. The compressed tablet according to claim 1, wherein said drugs are selected from the group consisting of diclofenac sodium, indomethacin, ibuprofen, ketoprofen, diflunisal, piroxicam, naproxen, flurbiprofen, tolmentin sodium, ampicillin, amoxycillin, cephradine, clavulanic acid, cephachlor, cephalexin, cloxacillin, erythromycin, their salts nitrofurantoin, nalidixic acid, oxolinic acid, pipemidic acid diazepam, nitrazepam, flurazepam, oxazepam, chlordiazepoxide, medazepam, lorazepam, diltiazem, trapidil, urapidil, benziodarone, dipiridamole, lidoflazine, naphthydrofuryl oxalate, perhexeline maleate, oxyfedrine hydrochloride, ephedrine, terfenadine, theophylline, L-dopa, carbidopa and chlorpheniramine.

7. The compressed tablet of claim 1 wherein said polymeric substances of said second layer may be further selected from the group consisting of poly(methyl vinyl ethers/maleic anhydride), ethylcellulose and methylcellulose.

* * * * *